US012752133B2

(12) United States Patent

Satir et al.

(10) Patent No.: US 12,752,133 B2
(45) Date of Patent: Oct. 6, 2026

(54) METHODS TO ENHANCE THE SAFETY OF TRANSCRANIAL ULTRASOUND STIMULATION PROCEDURES

(71) Applicant: Sanmai Technologies, PBC, Sunnyvale, CA (US)

(72) Inventors: Sarp Satir, Oakland, CA (US); Christopher Daft, Tucson, AZ (US); Quentin Owen Todd, Foster City, CA (US); Charles Frederick Cadieu, Burlingame, CA (US); Tomokazu Sato, Minneapolis, MN (US)

(73) Assignee: Sanmai Technologies, PBC, Sunnyvale, CA (US)

( * ) Notice: Subject to any disclaimer, the term of this patent is extended or adjusted under 35 U.S.C. 154(b) by 0 days.

(21) Appl. No.: 18/982,975

(22) Filed: Dec. 16, 2024

(65) Prior Publication Data

US 2025/0222281 A1 Jul. 10, 2025

Related U.S. Application Data

(60) Provisional application No. 63/572,577, filed on Apr. 1, 2024, provisional application No. 63/617,605, filed on Jan. 4, 2024.

(51) Int. Cl.
*A61N 7/00* (2006.01)

(52) U.S. Cl.
CPC ........ *A61N 7/00* (2013.01); *A61N 2007/0026* (2013.01); *A61N 2007/0073* (2013.01)

(58) Field of Classification Search
None
See application file for complete search history.

(56) References Cited

U.S. PATENT DOCUMENTS 11,839,455 B2 12/2023 Williams et al.
2008/0049994 A1* 2/2008 Rognin .................... G06T 7/35 382/128

(Continued)

FOREIGN PATENT DOCUMENTS

WO 2024/030928 A2 2/2024

OTHER PUBLICATIONS

Rodsetha et al., "A Novel Low-Cost Approach for Navigated Transcranial Magnetic Stimulation", Restorative Neurology and Neuroscience, DOI 10.3233/RNN-170751, vol. 35, Jan. 1, 2017, pp. 601-609.

(Continued)

*Primary Examiner* — Rochelle D Turchen
(74) *Attorney, Agent, or Firm* — Artegis Law Group, LLP

(57) ABSTRACT

Systems and methods for safety assessment before and during a transcranial ultrasound (TUS) procedure are described. A neuronavigation system is used to determine the probe's position and orientation. The probe's location and the subject's head MRI data are used to simulate the acoustic field within the subject's head. The acoustic field is overlaid on the MRI data and displayed to a clinician for evaluation. The phases of the transmit voltages are adjusted to optimize the location of the peak of the acoustic field to match the targets in the subject's brain. Before and during TUS, the spatial distribution of tissue temperature, MI, TIC, and $I_{SPTA}$ are computed and displayed to the clinician. Acoustic field changes due to the subject's movement are detected, and the TUS operation is terminated if the stimulated acoustic field becomes off-target. Monitoring circuits shut down the neuromodulation if parameters are out-of-range.

27 Claims, 7 Drawing Sheets

(56) References Cited

U.S. PATENT DOCUMENTS

| | | | | |
|---|---|---|---|---|
| 2014/0236061 | A1 | 8/2014 | Lee et al. | |
| 2016/0374710 | A1* | 12/2016 | Sinelnikov | A61B 17/3207 600/439 |
| 2018/0310917 | A1* | 11/2018 | Moehring | A61B 8/485 |
| 2019/0143136 | A1* | 5/2019 | Hunter | A61N 1/36 600/9 |
| 2021/0146119 | A1 | 5/2021 | Prouza et al. | |
| 2021/0370064 | A1* | 12/2021 | Murphy | G06N 3/0442 |
| 2022/0233886 | A1 | 7/2022 | Shoudy et al. | |

OTHER PUBLICATIONS

Boulanger et al., "Deep Learning Methods to Generate Synthetic CT From MRI In Radiotherapy: A Literature Review", Physica Medica, https://doi.org/10.1016/j.ejmp.2021.07.027, vol. 89, Sep. 2021, pp. 265-281.

Webb et al ., "Measurements of The Relationship Between CT Hounsfield Units and Acoustic Velocity and How it Changes with Photon Energy and Reconstruction Method", IEEE Trans Ultrason Ferroelectr Freq Control, DOI 10.1109/TUFFC.2018.2827899, vol. 65, No. 7, Jul. 2018, pp. 1111-1124.

Treeby et al., "Rapid Calculation of Acoustic Fields From Arbitrary Continuous-Wave Sources", Journal of the Acoustical Society of America, https://doi.org/10.1121/1.5021245, Jan. 30, 2018, pp. 529-537.

Clement et al., "The Role of Internal Reflection In Transskull Phase Distortion", Ultrasonics, https://doi.org/10.1016/S0041-624X(00)00052-4, vol. 39, Issue 2, Mar. 2001, pp. 109-113.

"How to Interpret the Ultrasound Output Display Standard for Diagnostic Ultrasound Devices", The American Institute of Ultrasound in Medicine, DOI 10.1002/jum. 15159, vol. 38, Nov. 17, 2019, pp. 3101-3105.

"IEC 60601-2-37 Consolidated version Revised", retrieved from https://webstore.iec.ch/publication/22634 on Jan. 15, 2025, 6 pages.

Pasquinelli et al., "Safety Of Transcranial Focused Ultrasound Stimulation: A Systematic Review of The State of Knowledge from Both Human and Animal Studies", Brain Stimulation, https://doi.org/10.1016/j.brs.2019.07.024, vol. 12, 2019, pp. 1367-1380.

* cited by examiner

METHODS TO ENHANCE THE SAFETY OF TRANSCRANIAL ULTRASOUND STIMULATION PROCEDURES

CROSS-REFERENCE TO RELATED APPLICATIONS

The application claims the priority benefit of U.S. Provisional Applications 63/617,605, entitled "METHODS TO ENHANCE THE SAFETY OF TRANSCRANIAL ULTRASOUND STIMULATION PROCEDURES" filed Jan. 4, 2024, and 63/572,577 entitled "TRANSCRANIAL ULTRASOUND PARAMETERS" filed Apr. 1, 2024. The subject matter of these related applications is hereby incorporated herein by reference.

TECHNICAL FIELD

This invention relates to the safe operation of transcranial ultrasound systems (TUS).

BACKGROUND

The safety of systems directing ultrasonic energy into the body has been the subject of intense investigation for decades. There were no FDA regulations about acoustic output during the initial years of ultrasound use in medicine. The technology was relatively new, and its biological effects were not fully understood.

The American Institute of Ultrasound in Medicine (AIUM) developed the Output Display Standard (ODS) to provide a framework for displaying information about the acoustic output of diagnostic systems. This initiative was in response to the increasing power outputs of ultrasound equipment and growing concerns about potential biological effects.

The FDA adopted AIUM's ODS in 1992. This marked a significant regulatory step, standardizing the measurement and reporting of ultrasound output through indices like the Mechanical Index (MI) and Thermal Index (TI). These parameters are now always displayed on diagnostic imaging systems. TIC—Thermal Index Cranial is the relevant thermal index for transcranial applications. The international medical device standard, IEC 60601-2-37, also implemented this approach with field characterization specified in the IEC 62359 standard.

In contrast to diagnostic systems, therapeutic ultrasonic systems are REGULATED on a per-device basis. These devices are evaluated and cleared based on their specific intended use. This includes assessing all parts of the device, including but not limited to acoustic output parameters like MI and TI. Manufacturers must provide comprehensive data showing the safety and efficacy of their device for the intended therapeutic application, including detailed information about the device's acoustic output and biological effects. Basic requirements for treatments such as thrombolysis, palliative pain relief in cancer, and lithotripsy are covered in IEC 60601-2-62. Only one type of treatment device is fully covered by an international standard, IEC 60601-2-5, for physical therapy ultrasound systems.

Without regulatory guidance or standards covering transcranial ultrasonic therapeutic devices, there is a need for procedures that ensure safe operation.

DETAILED DESCRIPTION

Systems and methods for safety assessment before and during a transcranial ultrasound (TUS) procedure are described. A neuronavigation system is used to determine the probe's position and orientation. The probe's location and the subject's head cranial volume imaging scan data are used to simulate the acoustic field within the subject's head. The acoustic field is overlaid on the MRI data and displayed to a clinician for evaluation. The phases of the transmit voltages are adjusted to optimize the location of the peak of the acoustic field to match the targets in the subject's brain. Before and during TUS, the spatial distribution of tissue temperature, MI, TIC, and $I_{SPTA}$ are computed and displayed to the clinician. Acoustic field changes due to the subject's movement are detected, and the TUS operation is terminated if the stimulated acoustic field becomes off-target. Monitoring circuits shut down the neuromodulation if parameters are out-of-range.

Multiple measures are implemented to enhance safety before and during TUS treatment. In one embodiment, based on the probe's location and the subject's head cranial volume imaging scan data e.g., MRI data, the acoustic field within the subject's head is simulated for a given set of transmit voltage phases. The acoustic field is superimposed on the anatomical data from cranial volume imaging scan data or MRI and displayed to the clinician. This allows the clinician to evaluate safety before the transcranial treatment. Using the display, the clinician can adjust the probe's location if it is not optimal for targeting the neuromodulation target. In another embodiment, the phases of the transmit voltages are adjusted to optimize the location of the peak of the acoustic field to match one or more desired targets in the subject's brain. Before and during the transcranial operation, the spatial distribution of tissue temperature, MI, TIC, $I_{SPTA}$, and $I_{SPPA}$ are computed, and the updated information is displayed to the clinician. The clinician can stop the treatment if the computed parameters are out-of-range. In another embodiment, acoustic field changes due to the subject's movement are detected, and the TUS operation is terminated if the stimulated acoustic field becomes off-target. In an embodiment, monitoring circuits shut down the neuromodulation or treatment if acoustic parameters such as $I_{SPTA}$ and $I_{SPPA}$ are out-of-range. In an embodiment, pulse-echo operations determine if the probe is acoustically coupled to the subject's head during the transcranial neuromodulation operation. In an embodiment, EEG is used to infer the acoustic coupling quality between the probe and the subject's scalp.

Figure 1:
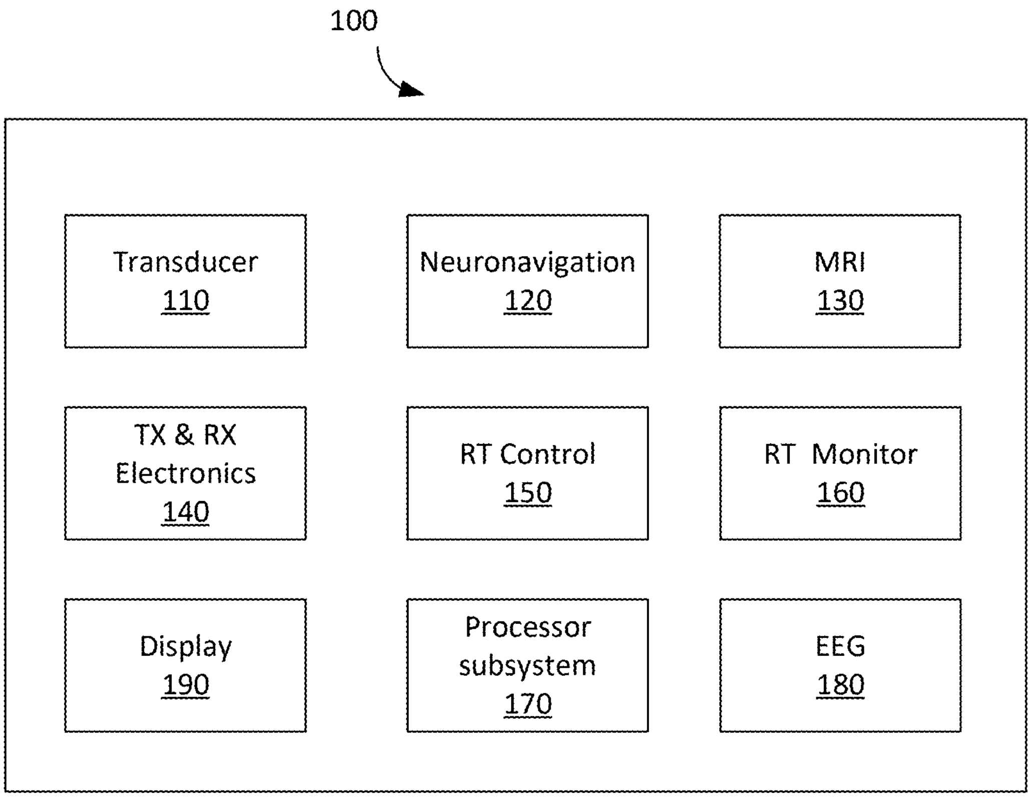
FIG. 1 shows an exemplary block diagram of a transcranial ultrasound System 100 used for safe transcranial operation.

FIG. 1 shows an exemplary block diagram of a transcranial ultrasound System 100 used for safe transcranial operation. Referring to FIG. 1, System 100 includes one or more ultrasound probe arrays or probes 110 used for neuromodulation. Annular array probes, or linear arrays, or matrix arrays can be used in implementations. Single element probes may also be used for neuromodulation, though in that case, electronic adjustment of the focal position is not possible.

Figure 2A:
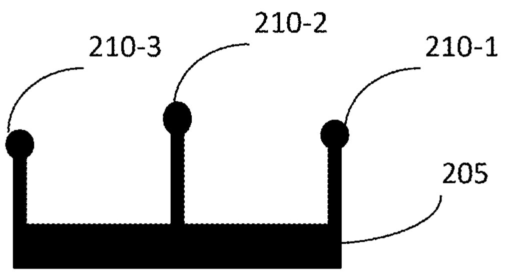
FIG. 2A and FIG. 2B show example components of Neuronavigation System 120 used in System 100.
Figure 2B:
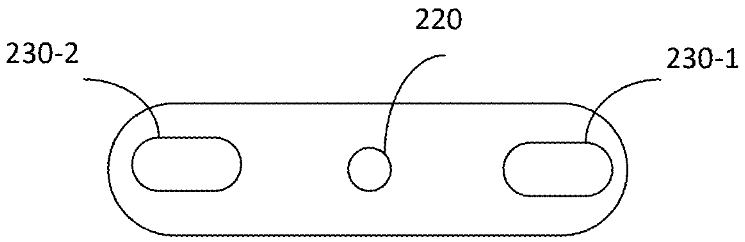

System 100 includes a neuronavigation system 120. Neuronavigation system 120 determines the angular orientation and the position (coordinates of the center) of probe 110. Infrared or LIDAR-based neuronavigation systems can be used. FIG. 2A and FIG. 2B show example components of stereoscopic infrared Neuronavigation System 120. Referring to FIG. 2A, structure 205 is rigidly attached to probe 110. Attached to structure 105 are several spherical balls 210 (three balls shown). Spherical balls 210 reflect light and have a fixed spatial relation. FIG. 2B shows infrared cameras 230 and LEDs 220. The light emitted by LED 220 is reflected by balls 210. The reflected light is captured by infrared cameras 230 (two cameras shown). System 100 determines probe 110's position and orientation from the images from cameras 230.

Referring to FIG. 1, the subject (or subject) obtains a cranial volume imaging scan data such as structural MRI of their head before an ultrasound treatment. A clinician (or operator of system 100) uses the cranial volume imaging scan data or MRI volume data 130 to locate the TUS neuromodulation target(s). Cranial volume imaging scan data or MRI scan data is processed to provide estimates of acoustic properties such as density and sound speed. This information is used to adjust the beam formation for the acoustic behavior of the skull so that a desirable TUS treatment region is achieved. RT (real-time) Control 150 and TX electronics 140 use this beam formation information to create the transmit voltages' phases and amplitudes for the elements of probe 110.

Target Location and Display

In an embodiment, System 100 reads the MRI 130 data and displays it on Display 190 to the clinician. The probe 110 position obtained by Neuronavigation 120 is overlaid on the cranial volume imaging scan data or MRI data. Acoustic properties from the cranial volume imaging scan data or MRI data are estimated. A simulation using the probe 110's position and orientation, the probe 110 drive signals, and the spatial distribution of the acoustic properties of the head is performed to derive the acoustic field, i.e., pressure and velocity distribution. The acoustic pressure is superimposed in color over the MRI data and displayed to the clinician on Display 190. This accurate field estimate enables the clinician to make a rigorous risk evaluation. The clinician can evaluate if the probe 110's location, or the specifics of the field distribution, poses a risk. The clinician can also evaluate if probe 110's location is optimal for targeting the neuromodulation target. More details on the display and target location are covered in the subsequent sections.

Processor subsystem 170 is used to perform the simulation. It may include CPUs, GPUs, AI processors, memory, hard disks, and interfaces like Ethernet, USB, Display Port, NVMe, PCIe, Wi-Fi, Bluetooth, and UARTs.

Electrical Faults

RT Monitor 160 monitors several electrical parameters to ensure the safe operation of System 100. In an implementation, RT Monitor 160 tracks acoustic parameters $I_{SPTA}$ (spatial peak temporal average intensity) and $I_{SPPA}$ (spatial peak pulse average intensity). If the acoustic parameters are out-of-range, the RT Monitor 160 stops generating transmit waveforms, aborts the neuromodulation, and informs the clinician.

Monitoring of Acoustic Coupling

A further concern is maintaining adequate mechanical contact between the probe 110 and the subject's scalp throughout the neuromodulation treatment period. Air must be excluded from the region between the probe and the scalp. A coupling gel often achieves this, though other materials are possible. Loss of contact is a perennial concern since it is impractical to attach the probe to the skull rigidly, and subject movement is always present.

Difficulties with acoustic coupling during transcranial neuromodulation are very common, and while not presenting a safety hazard to the subject, they can render the treatment ineffective. In an embodiment, the neuromodulation electronics are augmented with receivers to make pulse-echo operation possible using RX electronics 140. System 100 can periodically test for proper acoustic coupling, such as once per second. The received waveform differs substantially between a condition where sound is transmitted into the scalp and when an air gap between the probe and the scalp prevents ultrasound transmission.

Processor subsystem 170 distinguishes between these two waveforms. A large echo from the probe surface is received in the fault condition, with nothing following except reverberations. With good coupling, each element will receive less probe surface echo and will see subsequent strong echoes from the skull surfaces and the brain, forming a quite different waveform.

Information on the soundness of the acoustic contact derived from these waveforms can be obtained from each element. This means that probes with more elements provide more detail on which array parts may have impaired acoustic contact. When impaired acoustic contact is detected, System 100 notifies the clinician.

In an implementation, System 100 combines with an EEG (electroencephalography) or MEG (magnetoencephalography) subsystem 180 for closed-loop neuromodulation. In addition to its previously disclosed function in a closed-loop neuromodulation system, EEG subsystem 180 is here also used for measuring acoustic contact via the electrical impedance of the EEG electrodes. High impedances imply poor contact; if the electrodes are mounted near the acoustic probe elements and mechanically coupled to them, an abnormally high EEG impedance implies a problem with acoustic contact. When problematic acoustic contact is detected, System 100 notifies the clinician.

Definitions of Safety Parameters Used in Method for Enhanced Safety Mechanical Index (MI)

The Mechanical Index calculation of the risk of inertial (transient) and non-inertial (stable) cavitation uses the measured peak-rarefractional pressure in units of MPa, where an attenuated peak-rarefactional acoustic pressure $p_{ra}(z_{MI})$ at a depth $z_{MI}$ is derived from a measurement in water under laboratory conditions, assuming a coefficient to account for ultrasonic attenuation by tissue in the beam path:

$$MI = \frac{p_{ra}(z_{MI})}{C_{MI}\sqrt{f_w}}$$

where $f_w$ is the acoustic working frequency in MHz and $C_{MI}$ is a normalizing coefficient, 1 MPa·MHz$^{-1/2}$. MI is unitless and is limited to 1.9 in diagnostic imaging in the ODS. Increased pulse amplitudes result in proportionately higher MI values. The attenuation factor α derates the water measurement to produce a figure more representative of fields in soft tissues. The frequency dependence is to account for the increased difficulty in creating cavitation as the ultrasound center frequency increases.

Thermal Index TI (TIC is Used in the Transcranial Case)

The TI seeks to quantify where in the field is heated the most and by how much. In diagnostic imaging it is limited to a value of 6. It is computed by these formulae:

$$TIC = \frac{W_0/D_{eq}}{40\ \text{mW/cm}}$$

$W_0$: Total acoustic output power $D_{eq}$: Aperture diameter $$W_0 = \int\int \vec{I}(x, y, z)\cdot d\vec{S} = \int\int_S I_z(x, y)dS$$

Spatial Peak Temporal Average Intensity ($I_{SPTA}$)

$I_{SPTA}$ is the highest intensity (derated by a as above) measured at any point in the ultrasound beam averaged over the pulse repetition period. In diagnostic imaging, it is limited to 0.72 W/cm$^2$. If p is the pressure and u is the vector particle velocity of the ultrasound field, $$\vec{I}(x, y, z, t) = p(x, y, z, t)\times\vec{u}(x, y, z, t)$$

$$I(x, y, z, t) = \left|\vec{I}(x, y, z, t)\right|$$

$$I_{SPTA.3} = \frac{1}{T}\int_0^T I_3(x_{sp}, y_{sp}, z_{sp}, t)dt$$

Figure 3A:
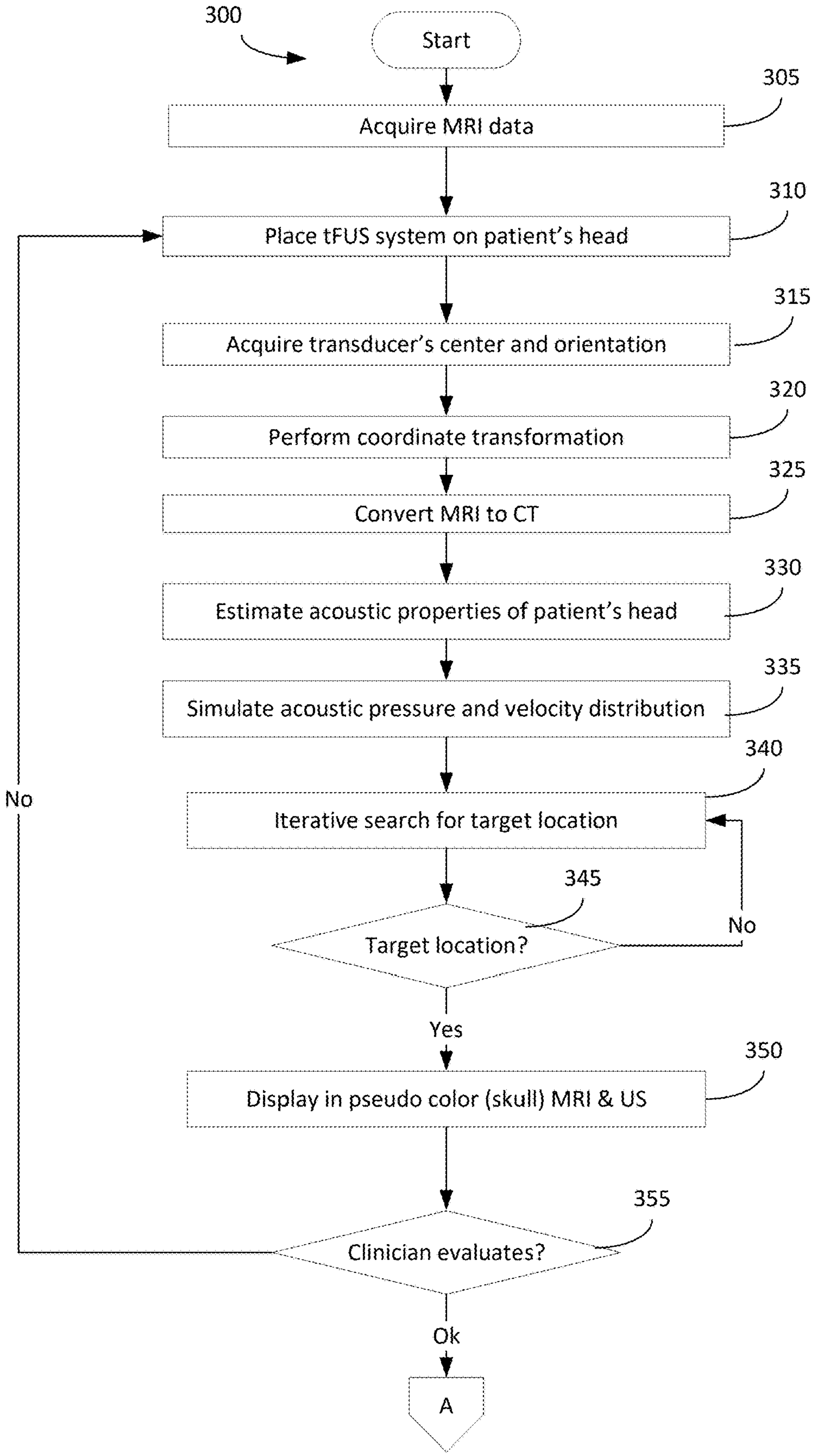
FIG. 3A and FIG. 3B show a continuous exemplary method 300, allowing for a COMPREHENSIVE SAFETY ASSESSMENT BEFORE AND DURING TRANSCRANIAL ULTRASOUND neuromodulation.
Figure 3B:
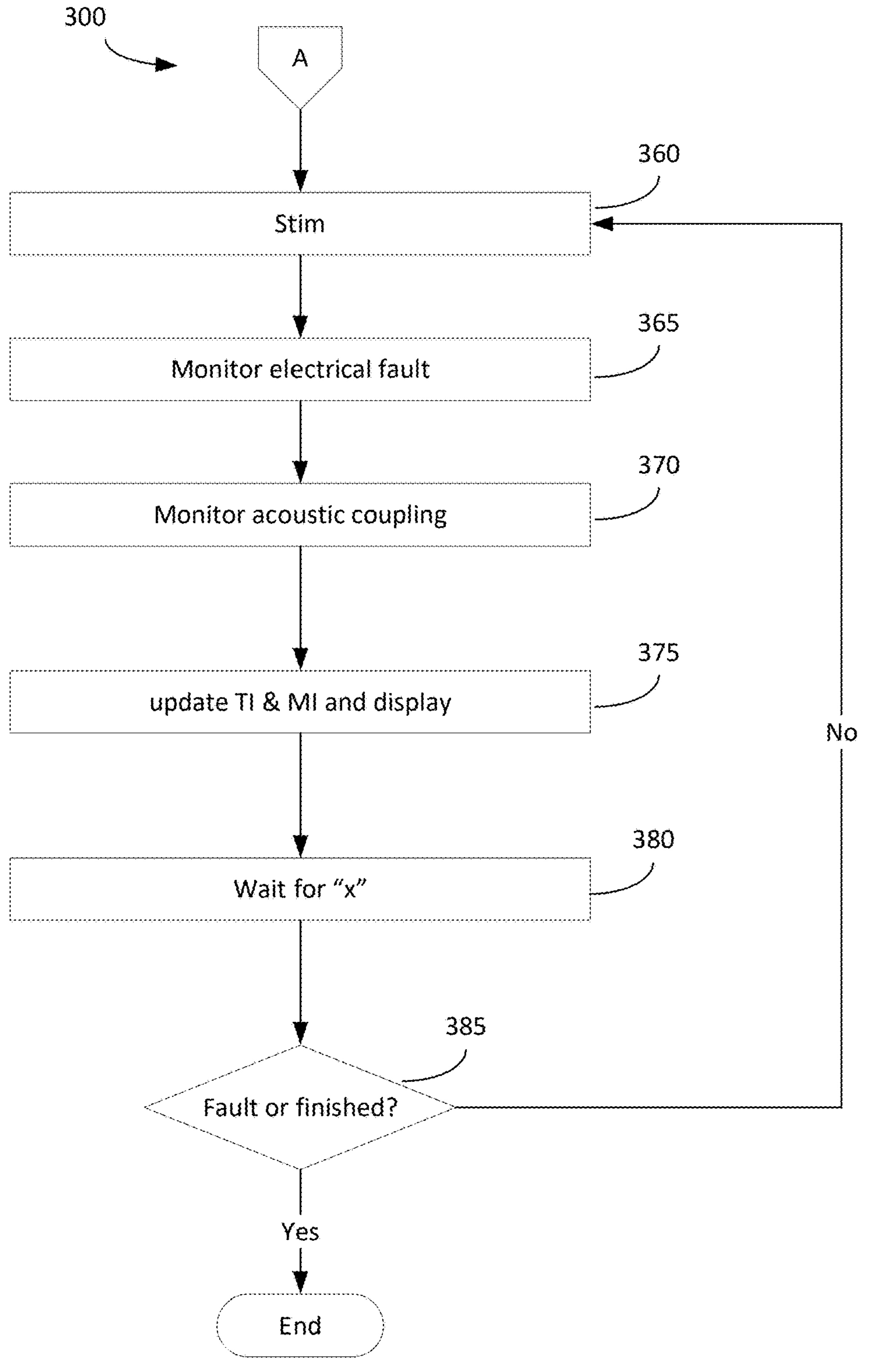

FIG. 3A and FIG. 3B show a continuous exemplary method 300, allowing for a comprehensive safety assessment before and during transcranial ultrasound neuromodulation. Although a method or flowchart may be described as a sequential process, the operations may be performed concurrently. In addition, the order of operations may be re-arranged, and some operations may be eliminated. Method 300 can be performed using System 100. Method 300 begins in Operation 305, where the subject or subject obtains a cranial volume imaging scan data or structural MRI of their head. The cranial volume imaging scan data or MRI volume data is loaded into System 100. System 100 displays the anatomical head data to the clinician using Display 190.

Referring to FIG. 3A, in Operation 310, probes 110 of System 100 are placed on the subject's head at an appropriate location. This location may be modified depending on operator evaluation 355.

In Operation 315, probe 110's location and orientation are acquired. In an implementation, the coordinates of the probe's center and its orientation are acquired using the Neuronavigation system 120 in a "Nasion-ear" coordinate system. This coordinate system is experimentally established by pointing a wand at the subject's Nasion, Left Preauricular Point, and Right Preauricular Point. Like the probe, the wand is attached to a set of reflecting balls so that the two infrared cameras in the neuronavigation system can record its position and orientation. After this calibration step, the probe's center and orientation are reported to the control software. System 100 generates the transmit phases and amplitudes for the elements of probe 110.

In operation 320, a coordinate transform is performed. Cranial volume imaging scan data or the MRI data acquired and the probe's location use different coordinate systems. Cranial volume imaging scan data or the MRI data is transformed into the nasion-ear coordinate system. The clinician finds the subject's Nasion, Left Preauricular, and Right Preauricular Points in the first coordinate system by navigating through the imaging volume and marking these fiducial points. The two coordinate systems can be mapped using rigid transformation methods such as Procrustes analysis. An example algorithm is described next.

Let the three points recorded in each coordinate system be A, B, and C, and the two coordinate systems be indicated by subscripts 1 and 2. Then the centroid is found by averaging the x, y, and z coordinates of the points separately for each system:

$$\text{Centroid}_1 = (A_1 + B_1 + C_1)/3$$

$$\text{Centroid}_2 = (A_2 + B_2 + C_2)/3$$

The translation vector is the difference between the centroids of the point sets. Next, translate all points in both systems so that their centroids are at the origin. This is done by subtracting the respective centroid from each point:

$$A_1' = A_1 - \text{Centroid}_1$$

and similarly for the 5 other points. The next step is to construct two matrices, one for each coordinate system, using the translated points as columns:

$$P_1 = [A_1'|B_1'|C_1']$$

$$P_2 = [A_2'|B_2'|C_2']$$

The rotation matrix R to best align the two sets of points can be found using singular value decomposition:

$$P_1 \cdot P_2^T = U\cdot\sum\cdot V^T$$

$$R = V\cdot U^T$$

The transformation P' for a point P in the first coordinate system can be found using the formula:

$$P' = R\cdot(P - \text{Centroid}_1) + \text{Centroid}_2$$

Figure 4:
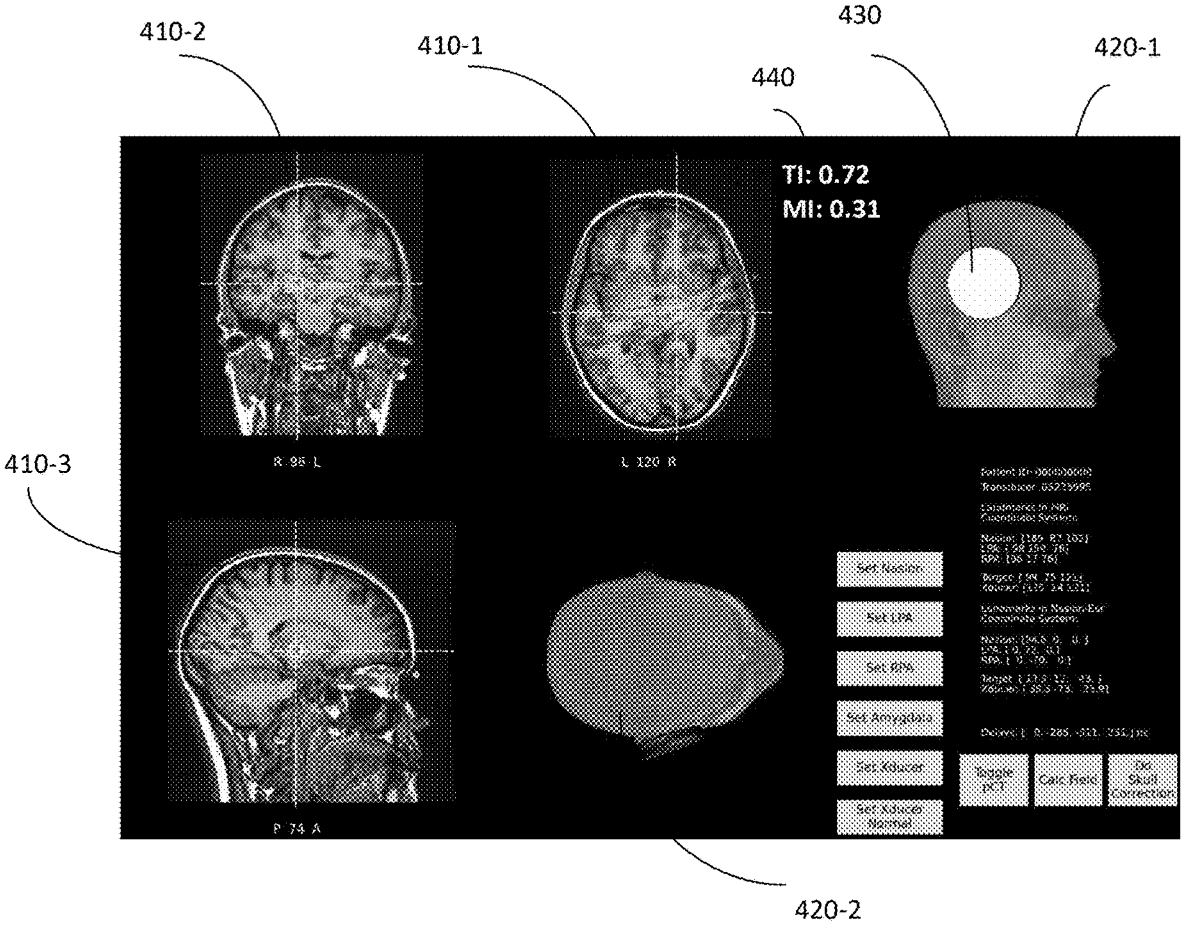
FIG. 4 and FIG. 5 are examples of the clinician's display showing the anatomical features of the subject's head with the acoustic field superimposed in color.

FIG. 4 shows an example of the clinician's display showing the anatomical features of the subject's head. This example shows the cranial volume or MRI data transformed into the nasion-ear coordinate system using the above algorithm, and displayed in grayscale. FIG. 4 shows three orthogonal planes 410 of data on the display and two rendered views of the outside 420 of the subject's head. FIG. 4 shows a rendering 430 of the probe 110.

Referring to FIG. 3A, in Operation 325, System 100 converts the cranial volume MRI data into a synthetic CT image. In Operation 330, System 100 estimates the acoustic properties of the subject's head by creating spatial distributions of Speed of Sound (SOS) and density values.

In Operation 335, a simulation in the nasion-ear coordinate system using:

1. the probe geometry or location
2. the drive signal to each probe element and
3. the spatial distribution of the acoustic properties of the head is performed to create an acoustic pressure and velocity distribution. The acoustic pressure is superimposed in color on the cranial volume or MRI and displayed to the clinician, as shown in FIG. 4. Estimated MI and TI values (440) are also displayed. The clinician may judge if the ultrasound field distribution presents any risks to structures in the subject's brain in this Operation.

Ultrasound propagation through the skull is complex. Because of this, the peak of the acoustic field may not appear at the target location when the simulation is run. Method 300 iterates between Operations 340 and 345 until the desired location is properly targeted with an effective ultrasound field distribution.

In an implementation where a simple acoustic focus is desired, a loss function L can be constructed as a ratio of power densities:

$$L(\varphi_i) = 1 - \frac{\text{power density at target}}{\text{power density at peak of acoustic field}}$$

This or other loss functions can be minimized using standard techniques that allow the acoustic field's peak to approach the center of the target region iteratively. The variables adjusted in the optimization are the transmit signal phases, qi. The iteration stops when the loss function is adequately close to 0. More sophisticated loss functions may be designed to create other field distributions than a simple focus as previously described. An optimal field distribution may instead be comprised of several focal points, or a distributed neuromodulation field without a distinct focus.

Once the optimization described here is completed, the transmit signal phases are fully defined.

Figure 5:
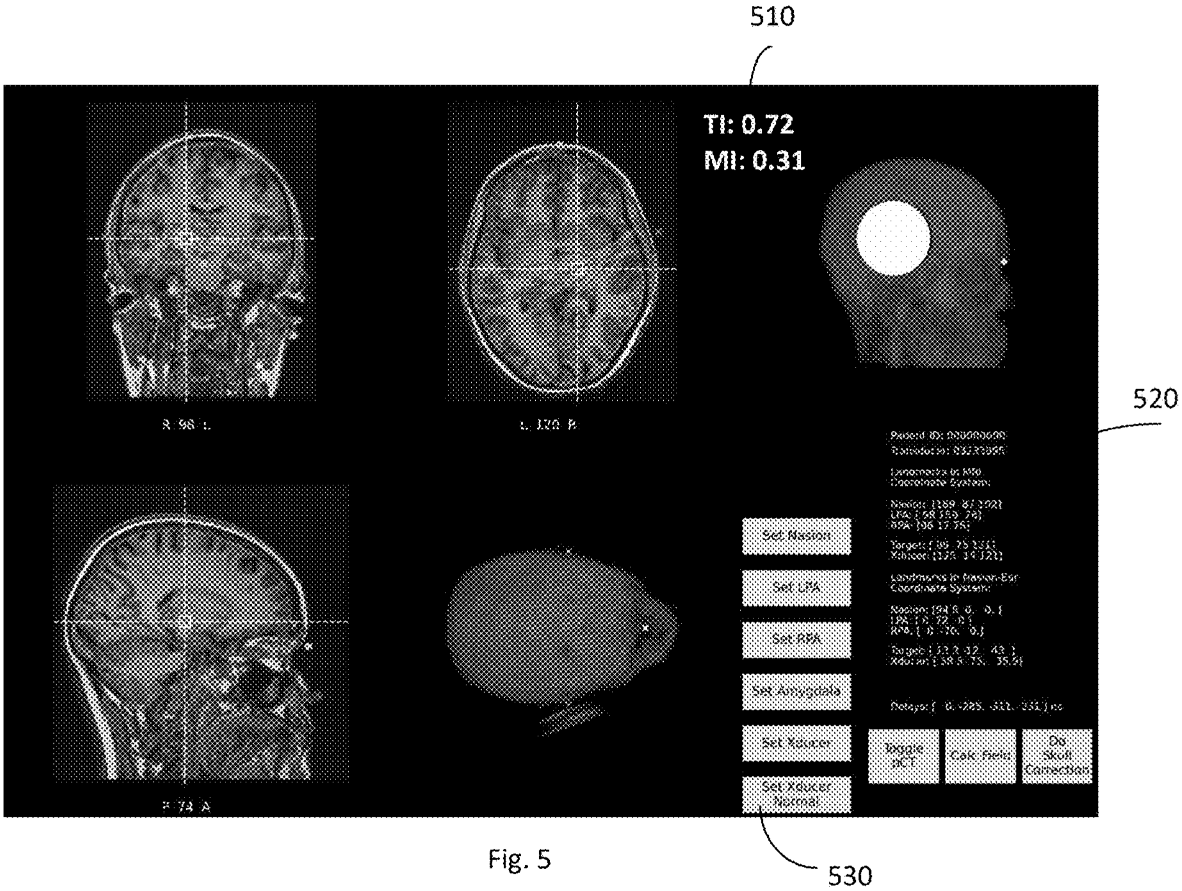

In Operation 350, the ultrasound field in color is overlaid over the synthetic CT data and displayed to the clinician on Display 190. FIG. 5 shows an example where the acoustic field is overlaid on the anatomical data as in FIG. 4. However, FIG. 5's anatomical information is shown as estimated acoustic properties, such as density and sound speed, rather than MRI contrast. For example, FIG. 5 shows sound speed. Here, high speeds in the skull are evident in the colors displayed. MRI contrast as shown in FIG. 4 is typically dependent on nuclear spin decay times and results in T1-weighted or T2-weighted images.

In FIG. 5, the target location is marked by the crossing of the dotted white lines which move responding to the operator's selection. The Nasion, Left Preauricular, and Right Preauricular Points are yellow, red, and green dots, respectively. The location of the neuromodulation probe is indicated by the white circle. TI and MI are displayed. FIG. 5 includes various informational text messages 520 showing the coordinates of the target, probe, Left Preauricular, Right Preauricular Points, etc. UI elements 530 are also provided for the clinician to interact with System 100.

Referring to FIG. 3A, in Operation 355, the clinician evaluates the results displayed on Display 190 for risks, etc. While the MI and TI values from diagnostic imaging are helpful initial guides, having an accurate field estimate enables a more rigorous evaluation of the risk of the treatment. If the operator finds that the initial probe location presents safety issues, other probe locations can be evaluated to determine improvements to subject safety. If the probe can be mechanically angled with a spacer or steered by electronic phasing, more probe locations that will reach the target may be available. If the clinician approves, the following Operation in the method is Operation 360. If the clinician disapproves, the method reverts to Operation 310, where the probe 110 is moved to a more appropriate location on the subject's head. In an implementation, the clinician changes the probe's position on the head, and the system alters the phase and amplitude of the drive signals to the elements of probe 110 to see if the new probe position and location alleviates the risks identified by the clinician.

Referring to FIG. 3B, in Operation 360, the system performs neuromodulation on the subject. Operations 365, 370, and 375 can be performed concurrently where the Method monitors for electrical faults and acoustic coupling and calculates and updates TI & MI values on Display 190.

Electrical Monitoring

In Operation 365, the method monitors several electrical parameters to ensure the safe operation of System 100. In an implementation, acoustic parameters $I_{SPTA}$ (spatial peak temporal average intensity) and $I_{SPPA}$ (spatial peak pulse average intensity) are monitored. If the parameters are out-of-range, the Method stops generating transmit waveforms, aborts the neuromodulation, and informs the clinician. The RT monitor 160 in System 100 may monitor electrical parameters.

Monitoring of Acoustic Coupling

In Operation 370, the Method monitors the acoustic coupling between probe 110 and the subject's scalp. Losing contact is problematic since it is impractical to attach the probe to the skull rigidly, and subject movement is always present. Difficulties with contact are common, and while not presenting a safety hazard to the subject, they can render the treatment ineffective. Acoustic coupling is monitored using pulse-echo ultrasound or EEG. In an implementation, the neuromodulation electronics are augmented with receivers to make the pulse-echo operation possible by RX electronics 140. The received waveform differs substantially between a condition where sound is transmitted into the scalp and when an air gap between the probe and the scalp prevents ultrasound transmission.

Processor subsystem 170 distinguishes between these two waveforms. A large echo from the probe surface is received in the fault condition, with nothing following except reverberations. With good coupling, each element will receive less probe surface echo and subsequent strong echoes from the skull surfaces and the brain, forming a different waveform. Information on the soundness of the acoustic contact derived from these waveforms can be obtained from each element. This means that probes with more elements provide more detail on which array parts may have impaired acoustic contact. When impaired acoustic contact is detected, Method 300 notifies the clinician.

In an implementation, EEG subsystem 180 may be used for measuring acoustic contact. This approach uses a measurement of the electrical impedance of the EEG electrodes. High impedances imply poor contact. If the electrodes are mounted near the acoustic probe, and mechanically attached to it, an abnormally high EEG impedance indicates a problem with acoustic contact. When impaired acoustic contact is detected, Method 300 notifies the clinician.

Estimation of Tissue Temperature

In Operation 375, Method 300 updates MI and TI on Display 190. The clinician can view the updated TI and MI to determine any safety issues and stop the neuromodulation if required. In an implementation, a safe operating range is established for TI and MI, and if the values are out-of-range, the Method stops the neuromodulation. In an implementation, the Pennes bioheat equation may be used since the output of the pseudospectral field simulation provides the spatial distribution of pressure and velocity, from which the rate of heat generation Q(x,y,z) can be computed.

The effect of this heat deposition changes tissue temperature T as described by the Pennes bioheat equation:

$$\rho C \frac{\partial T}{\partial t} = \nabla \cdot (k \nabla T) + \rho_b C_b \omega_b (T_a - T) + Q(x, y, z)$$

where:

- t is time
- p is the density of the tissue.
- C is the specific heat capacity of the tissue.
- k is the thermal conductivity of the tissue.
- $\nabla \cdot (k \nabla T)$ represents the heat conduction within the tissue.
- $\rho_b$ is the blood density.
- $C_b$ is the specific heat capacity of blood.
- $\omega_b$ is the blood perfusion rate.
- $T_a$ is the arterial blood temperature.

After solving the bioheat equation, an estimated temperature map may be superimposed on the MRI data, similar to the acoustic pressure map shown in FIG. 5. Similarly, the Method can compute the spatial distribution of MI, TIC, and $I_{SPTA}$ and superimpose the distribution of any of those parameters over the MRI data.

In Operation 380, the Method waits for a period, for example, 1 second. This Operation is required to monitor acoustic coupling. Electrical fault monitoring and TI & MI updates are performed continuously.

In Operation 385, the Method checks for electrical or acoustic fault conditions, or if the duration of the neuromodulation has finished. In case of a fault or if neuromodulation has finished, the Method ends. If there are no faults and neuromodulation has not been finished, the following operation is Operation 360, and the neuromodulation continues, and the Method monitors for faults and acoustic coupling.

Ultrasound Parameters

Figure 6A:
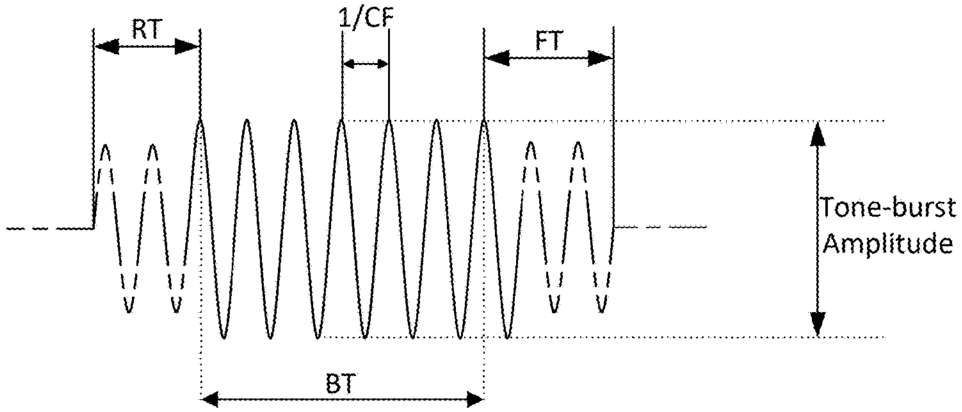
FIGS. 6A, 6B, and 6C are example waveforms illustrating the key parameters used for neuromodulation by System 100.

In addition to $I_{SPTA}$, $I_{SPPA}$, MI, TI, etc., System 100 and Method 300 ensure that key ultrasound parameters are within a safe range. TUS System 100 generates ultrasound waves consisting of a burst (a tone-burst) of pulses. The tone-burst has a duration BT (Burst Time) and consists of pulses with frequency CF (Center Frequency, also called Acoustic frequency AF). A tone-burst has amplitude control at the start and end of the burst, illustrated in FIG. 6A. FIG. 6A shows the pulse's Center Frequency (shown as 1/CF, the pulse period), RT (Rise Time), FT (Fall Time), and Burst Time (BT). RT (Rise Time) and FT (Fall Time) are measured in cycles (1/CF, multiples of pulse period) and are a measure of the time taken for the burst to start (reach maximum Amplitude) or stop.

Figure 6B:
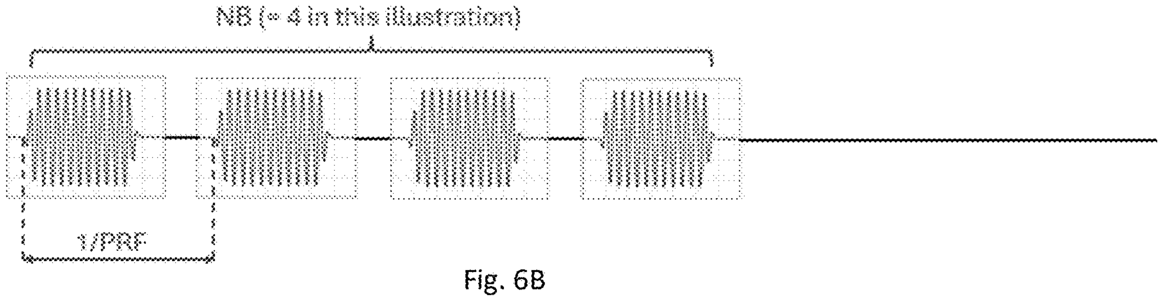
Figure 6C:
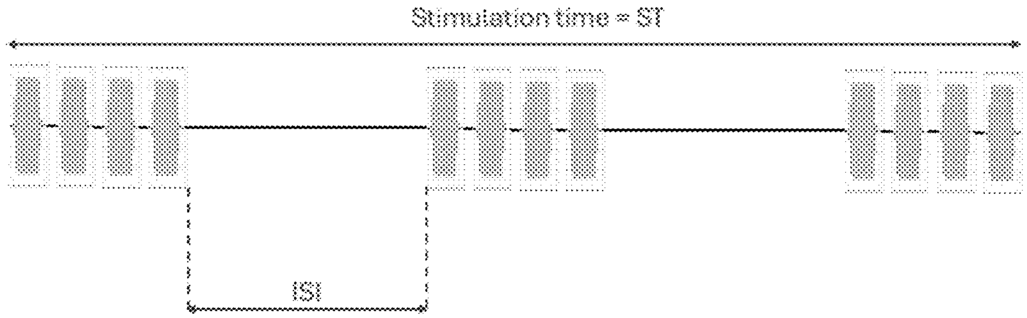

The burst is followed by a quiescent time and repeated for NB (number of bursts). The tone bursts are repeated at PRF (pulse repetition frequency). FIG. 6B illustrates the number of bursts (NB) and pulse repetition frequency (PRF). FIG. 6B shows a NB of four. This sequence is repeated for ST (neuromodulation time) with ISI (Inter Neuromodulation Intervals) intervals. Ultrasound is not transmitted during the ISI. FIG. 6C shows the total neuromodulation time (ST) and inter-neuromodulation interval (ISI). Waveform generators (in TX Electronics 140) generate neuromodulation waveforms within the specified safe range. In an implementation, RT Monitor 160 monitors the ultrasound neuromodulation parameters to ensure System 100's operation is within a safe range. Table 1 below summarizes the ranges allowed by System 100. Operation 365 in Method 300 ensures that the ultrasound parameters are within the range.

TABLE 1

| Parameter | Unit | Minimum | Maximum |
|---|---|---|---|
| Center Frequency CF | MHz | 0.2 | 3.0 |
| Rise Time | pulse periods | 0 | 10 |
| Fall Time | pulse periods | 0 | 10 |
| Burst Time BT | ms | 0.05 | 30,000 |
| Number of bursts NB | | 1 | 10,000 |
| Pulse repetition frequency PRF | Hz | 0.2 | 1,000 |
| Inter-neuromodulation interval ISI | s | 0.01 | 60 |
| Total neuromodulation time ST | s | 1 | 1,000 |

1. In some embodiments, a method for operation of a transcranial ultrasound device comprises obtaining a cranial volume imaging scan of a subject, estimating acoustic properties of a head of a subject based on the cranial volume imaging scan data, acquiring a location of a probe from based on data from a neuronavigation system and the cranial volume imaging scan, generating a simulated acoustic field within the head based on the acoustic properties, the location of the probe, and a set of transmit voltage phases utilized for the probe, and displaying the simulated acoustic field in a user interface, wherein the simulated acoustic field is overlaid onto anatomical data associated with the MRI.
2. The method of clause 1, wherein phases of the set of transmit voltages are adjusted based on a location of a peak of the acoustic field to correspond to at least one desired target within a brain of the subject.
3. The method of clauses 1 or 2, wherein the simulated acoustic field is further based on a spatial distribution of at least one of tissue temperature, spatial peak temporal average intensity, and a thermal index for transcranial applications.

4. The method of any of clauses 1-3, wherein the simulated acoustic field is updated in response to movement of the subject.
5. The method of any of clauses 1-4, further comprising displaying, in the user interface, an updated simulated acoustic field based on an updated spatial distribution of at least one of tissue temperature, spatial peak temporal average intensity, and a thermal index for transcranial applications.
6. The method of any of clauses 1-5, further comprising performing neuromodulation of the subject using the probe based on the set of transmit voltage phases.
7. The method of any of clauses 1-6, further comprising terminating the neuromodulation in response to an updated simulated acoustic field showing a value outside a clinically acceptable range, wherein the updated simulated acoustic field is generated in response to movement of the subject.
8. The method of any of clauses 1-7, where the center frequency of neuromodulation of the subject is between 0.2 and 3.0 MHz.
9. The method of any of clauses 1-8, where a rise time corresponding to neuromodulation of the subject is between 0 and 10 cycles.
10. The method of any of clauses 1-9, where the fall time corresponding to neuromodulation of the subject is between 0 and 10 cycles (pulse period).
11. The method of any of clauses 1-10, where the burst time (BT) corresponding to neuromodulation of the subject is between 50 μs and 30 s.
12. The method of any of clauses 1-11, where the number of bursts (NB) corresponding to neuromodulation of the subject is between 1 and 10,000.
13. The method of any of clauses 1-12, where the pulse repetition frequency corresponding to neuromodulation of the subject is between 0.2 and 1,000 Hz.
14. The method of any of clauses 1-13, where the inter-neuromodulation interval corresponding to neuromodulation of the subject is between 0.01 and 60 s.
15. The method of any of clauses 1-14, where the total neuromodulation time corresponding to neuromodulation of the subject is between 1 and 1,000 s.
16. In some embodiments, a system comprises a cranial volume imaging scan data) scanner, an ultrasound probe comprising a plurality of neuromodulation elements configured to deliver neuromodulation signals, probe drive electronics coupled to the ultrasound probe, the probe drive electronics configured to adjust a phase of the signals provided to the ultrasound probe, a neuronavigation system, and at least one processor executing an application that, when executed, causes the at least one processor to at least obtain a cranial magnetic resonance image (MRI) of a subject, estimate acoustic properties of a head of the subject based on the cranial volume imaging scan data, acquire a location of a probe from based on data from the neuronavigation system and the cranial volume imaging scan data, generate a simulated acoustic field within the head based on the acoustic properties, the location of the probe, and a set of transmit voltage phases utilized for the probe, and display the simulated acoustic field in a user interface, wherein the simulated acoustic field is overlaid onto anatomical data associated with the MRI.
17. The system of clause 16, wherein the probe drive electronics shut down neuromodulation signals delivered by the ultrasound probe in response to the neuromodulation signals deviating from specified values.
18. The system of clauses 16 or 17, wherein the probe drive electronics perform pulse-echo operation to determine whether the neuromodulation probes remain acoustically coupled to a subject's head during treatment.
19. The system of any of clauses 16-18, wherein application infers quality of acoustic coupling of the neuromodulation probes based on impedances of EEG electrodes associated with the neuromodulation probes.
20. The system of any of clauses 16-19, wherein the application causes the at least one processor to at least generate a simulated acoustic field within a subject head based on acoustic properties, a location of the probe, and a set of transmit voltage phases utilized for the probe, and display a simulated acoustic field in a user interface, wherein the simulated acoustic field is overlaid onto anatomical data associated with the cranial volume imaging scan data.
21. The system of any of clauses 16-20, wherein the application causes the ultrasound probe to provide neuromodulation based on a set of transmit voltages from the probe drive electronics.
22. The system of any of clauses 16-21, where the rise time corresponding to the neuromodulation is between 0 and 10 cycles (pulse period).
23. The system of any of clauses 16-22, where the fall time corresponding to the neuromodulation is between 0 and 10 cycles (pulse period).
24. The system of any of clauses 16-23, where the burst time (BT) corresponding to the neuromodulation is between 50 μs and 30 s.
25. The system of any of clauses 16-24, where the number of bursts (NB) corresponding to the neuromodulation is between 1 and 10,000.
26. The system of any of clauses 16-25, where the pulse repetition frequency corresponding to the neuromodulation is between 0.2 and 1,000 Hz.
27. The system of any of clauses 16-26, where the inter-neuromodulation interval corresponding to the neuromodulation is between 0.01 and 60 s.
28. The system of any of clauses 16-27, where the total neuromodulation time corresponding to the neuromodulation is between 1 and 1,000 s.

Any and all combinations of any of the claim elements recited in any of the claims and/or any elements described in this application, in any fashion, fall within the contemplated scope of the present invention and protection.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "module," a "system," or a "computer." In addition, any hardware and/or software technique, process, function, component, engine, module, or system described in the present disclosure may be implemented as a circuit or set of circuits. Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine. The instructions, when executed via the processor of the computer or other programmable data processing apparatus, enable the implementation of the functions/acts specified in the flowchart and/or block diagram block or blocks. Such processors may be, for example, general purpose processors, special-purpose processors, application-specific processors, or field-programmable gate arrays.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the preceding is directed to embodiments of the present disclosure, other and further embodiments of the disclosure may be devised without departing from the basic scope thereof, and the scope thereof is determined by the claims that follow.

What is claimed is:

1. A method for operation of a transcranial ultrasound device comprising:

obtaining a cranial volume imaging scan data of a subject;

estimating acoustic properties of a head of the subject based on the cranial volume imaging scan data;

acquiring a location of a probe based on data from a neuronavigation system;

performing a coordinate transformation of the cranial volume imaging scan data into a nasion-ear coordinate system established by the neuronavigation system;

generating a simulated acoustic field within the head in real-time based on the acoustic properties, the location of the probe, and a set of transmit voltage phases utilized for the probe;

displaying the simulated acoustic field in a user interface, wherein the simulated acoustic field is overlaid onto anatomical data associated with the cranial volume imaging scan data to illustrate whether the location the of the probe requires correction; and iteratively adjusting the set of transmit voltage phases in response to the real-time simulated acoustic field to align a peak of the simulated acoustic field with a desired target within the brain.

2. The method of claim 1, wherein the set of transmit voltage phases are adjusted based on a location of a peak of the simulated acoustic field to correspond to at least one desired target within a brain of the subject.

3. The method of claim 1, wherein the simulated acoustic field is further based on a spatial distribution of at least one of a tissue temperature, a spatial peak temporal average intensity, and a thermal index for transcranial applications.

4. The method of claim 1, wherein the simulated acoustic field is updated in response to movement of the subject.

5. The method of claim 1, further comprising displaying, in the user interface, an updated simulated acoustic field based on an updated spatial distribution of at least one of tissue temperature, spatial peak temporal average intensity, and a thermal index for transcranial applications.

6. The method of claim 1, further comprising performing neuromodulation of the subject using the probe based on the set of transmit voltage phases.

7. The method of claim 6, further comprising terminating the neuromodulation in response to an updated simulated acoustic field showing a value outside a clinically acceptable range, wherein the updated simulated acoustic field is generated in response to movement of the subject.

8. The method of claim 6, where a center frequency of neuromodulation of the subject is between 0.2 and 3.0 MHz.

9. The method of claim 6, where a rise time corresponding to neuromodulation of the subject is between 0 and 10 cycles.

10. The method of claim 6, where a fall time corresponding to neuromodulation of the subject is between 0 and 10 cycles (pulse period).

11. The method of claim 6, where a burst time (BT) corresponding to neuromodulation of the subject is between 50 μs and 30 s.

12. The method of claim 6, where a number of bursts (NB) corresponding to neuromodulation of the subject is between 1 and 10,000.

13. The method of claim 6, where a pulse repetition frequency corresponding to neuromodulation of the subject is between 0.2 and 1,000 Hz.

14. The method of claim 6, where an inter-neuromodulation interval corresponding to neuromodulation of the subject is between 0.01 and 60 s.

15. The method of claim 6, where a total neuromodulation time corresponding to neuromodulation of the subject is between 1 and 1,000 s.

16. A system comprising:

a cranial volume imaging scan scanner configured to obtain a cranial volume image scan data of a subject;

at least one ultrasound probe comprising a plurality of ultrasound elements configured to deliver neuromodulation to the subject;

ultrasound probe drive electronics coupled to the ultrasound probe, the ultrasound probe drive electronics configured to adjust a phase of signals provided to the at least one ultrasound probe;

a neuronavigation system configured to acquire probe orientation in a nasion-ear coordinate system;

an electroencephalography (EEG) system with one or more EEG electrodes; and at least one processor executing an application that, when executed, causes the at least one processor to at least:

estimate acoustic properties of a head of the subject based on the cranial volume image scan data;

acquire a location of the at least one ultrasound probe based on data from the neuronavigation;

transform the cranial volume imaging scan data into the nasion-ear coordinate system;

generate a simulated acoustic field within the head in real-time based on the acoustic properties, the location of the at least one ultrasound probe, and a set of transmit voltage phases utilized for the at least one ultrasound probe to illustrate whether the location the of the probe requires correction; and display the simulated acoustic field in a user interface, wherein the simulated acoustic field is overlaid onto anatomical data associated with the cranial volume image scan data.

17. The system of claim 16, further configured to perform neuromodulation on the subject and wherein the ultrasound probe drive electronics shut down signals delivered by the at least one ultrasound probe in response to the acoustic properties deviating from specified values.

18. The system of claim 16, wherein the ultrasound probe drive electronics perform pulse-echo operation to determine whether the at least one ultrasound probe remains acoustically coupled to a head of the subject during treatment.

19. The system of claim 16, wherein the application infers quality of acoustic coupling of the at least one ultrasound probe based on impedances of EEG electrodes.

20. The system of claim 16, wherein the application causes the at least one ultrasound probe to provide neuromodulation based on a set of transmit voltages from the ultrasound probe drive electronics.

21. The system of claim 20, where a rise time corresponding to the neuromodulation is between 0 and 10 cycles (pulse period).

22. The system of claim 20, where a fall time corresponding to the neuromodulation is between 0 and 10 cycles (pulse period).

23. The system of claim 20, where a burst time (BT) corresponding to the neuromodulation is between 50 μs and 30 s.

24. The system of claim 20, where a number of bursts (NB) corresponding to the neuromodulation is between 1 and 10,000.

25. The system of claim 20, where a pulse repetition frequency corresponding to the neuromodulation is between 0.2 and 1,000 Hz.

26. The system of claim 20, where a inter-neuromodulation interval corresponding to the neuromodulation is between 0.01 and 60 s.

27. The system of claim 20, where a total neuromodulation time corresponding to the neuromodulation is between 1 and 1,000 s.

* * * * *